US007700298B2

(12) United States Patent
Wissel

(10) Patent No.: US 7,700,298 B2
(45) Date of Patent: *Apr. 20, 2010

(54) METHODS FOR DETERMINATION OF AN ANALYTE

(75) Inventor: Thomas Wissel, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 539 days.

This patent is subject to a terminal disclaimer.

(21) Appl. No.: 11/355,316

(22) Filed: Feb. 16, 2006

(65) Prior Publication Data

US 2007/0026459 A1    Feb. 1, 2007

Related U.S. Application Data

(63) Continuation of application No. 08/466,881, filed on Jun. 6, 1995, now Pat. No. 7,029,856, which is a continuation of application No. 08/173,939, filed on Dec. 28, 1993, now abandoned, which is a continuation of application No. 07/805,688, filed on Dec. 12, 1991, now abandoned.

(30) Foreign Application Priority Data

Dec. 21, 1990 (DE) .............................. P 40 41 080

(51) Int. Cl.
G01N 33/53 (2006.01)
G01N 33/553 (2006.01)
G01N 33/544 (2006.01)

(52) U.S. Cl. .................. 435/7.1; 435/962; 436/526; 436/528; 436/529; 436/530; 436/531; 436/537; 436/800; 436/804; 436/805

(58) Field of Classification Search .................. 435/7.1, 435/962; 436/526, 528, 529, 530, 531, 537, 436/800, 804, 805
See application file for complete search history.

(56) References Cited

U.S. PATENT DOCUMENTS

| 3,933,997 | A | | 1/1976 | Hersh et al. |
| 3,970,518 | A | | 7/1976 | Giaever |
| 4,018,886 | A | | 4/1977 | Giaever |
| 4,041,146 | A | | 8/1977 | Giaever |
| 4,231,999 | A | * | 11/1980 | Carlsson et al. ............... 435/7.8 |
| 4,297,337 | A | | 10/1981 | Mansfield et al. |
| 4,358,388 | A | | 11/1982 | Daniel et al. |
| 4,554,088 | A | | 11/1985 | Whitehead et al. |
| 4,576,912 | A | * | 3/1986 | Yaverbaum et al. ........... 435/7.1 |
| 4,628,037 | A | | 12/1986 | Chagnon et al. |
| 4,654,267 | A | | 3/1987 | Ugelstad et al. |
| 4,687,734 | A | | 8/1987 | Chester |
| 4,780,421 | A | | 10/1988 | Kameda et al. |
| 4,891,324 | A | | 1/1990 | Pease et al. |
| 4,927,769 | A | | 5/1990 | Chang et al. |
| 4,971,904 | A | | 11/1990 | Luddy |
| 5,268,306 | A | | 12/1993 | Berger et al. |
| 5,279,936 | A | | 1/1994 | Vorpahl |
| 6,002,007 | A | | 12/1999 | Kinkel et al. |
| 7,029,856 | B1 | * | 4/2006 | Wissel ........................ 435/7.1 |

FOREIGN PATENT DOCUMENTS

| CA | 1 341 402 | | 11/2002 |
| DE | 38 42 125 | | 6/1989 |
| EP | 0 030 087 | | 6/1981 |
| EP | 0 038 181 | | 10/1981 |
| EP | 0 136 126 | | 4/1985 |
| EP | 0 149 565 | | 7/1985 |
| EP | 0149565 | * | 7/1985 |
| EP | 0 177 191 | | 4/1986 |
| EP | 0 219 352 | | 4/1987 |
| EP | 0 257 541 | | 3/1988 |
| EP | 0 281 390 | | 9/1988 |
| EP | 0 330 050 | | 8/1989 |
| EP | 0 331 127 | | 9/1989 |
| EP | 0 371 265 A1 | | 6/1990 |
| EP | 0 488 152 | | 6/1992 |
| JP | 02-198361 | | 8/1990 |

OTHER PUBLICATIONS

Baum et al, "Affinity Chromatography", in, Immobilized Enzymes, Antigens, Antibodies, and Peptides, Howard H. Weetall, ed., Marcel Dekker, Inc. NY, NY (1975), pp. 451-454.*
Hunter et al., Immunoassays for clinical chemistry, $2^{nd}$ Edition, Chapter 4.3, p. 147-162, Churchill Livingstone (1983).
Kinkel et al., "Synthesis and properties of new luminescent acridinium-9-carboxylic acid derivatives and their application in luminescence immunoassays (LIA)," *Journal of Bioluminescence and Chemiluminescence*, 4:136-139 (1989).
Nargessi et al., "Solid-phase fluoroimmunoassay of human albumin in biological fluids," *Clinica Chimica Acta*, 89:455-460 (1978).
Piran et al., "Immunochemiluminometric assay of creatine kinase MB with a monoclonal antibody to the MB isoenzyme," *Clin. Chem.*, 33:1517-1520 (1987).
Sturgess et al., "Chemiluminescent labeled-antibody assay for thyroxin in serum, with magnetic separation of the solid-phase," *Clin. Chem.*, 32:532-535 (1986).
Weerasekera et al., "Monitoring ovarian function by a solid-phase chemiluminescence immunoassay," *Acta Endocrinologica*, 101:254-263 (1982).
Decision of the Technical Board of Appeal 3.3.08 dated Nov. 8, 2007 revoking European Patent No. 0492499.
"Enzyme Immunoassays in Diagnostic Medicine," by A. Voller et al., Bull World Health Organization, vol. 53, pp. 55-65, 1976.
"[37] Monitoring Specific Protein-Binding Reactions with Chemiluminescence," Methods in Enzymology, vol. LVII, for Academic Press Inc., New York, pp. 424-445, (1978).

(Continued)

*Primary Examiner*—Rodney P. Swartz
(74) *Attorney, Agent, or Firm*—Finnegan, Henderson, Farabow, Garrett & Dunner, LLP

(57) ABSTRACT

The invention relates to analytical methods in which the partition of a labeled substance between a liquid and a solid phase is determined. The assays include solid-phase reagents which can be particulate or monolithic such as, for example, a coated tube. Assays of this type are known per se to the person skilled in the art and include immunoassays and immunometric assays.

11 Claims, 3 Drawing Sheets

OTHER PUBLICATIONS

Clin. Chem. vol. 29, No. 8, pp. 1474-1479 (1983), "Acridinium Esters as High-Specific-Activity Labels in Immunoassay" by Ian Weeks, et al.

Baum et al., "Affinity Chromatography," In *Immobilized Enzymes, Antigens, Antibodies, and Peptides*, Howard H. Weetall, Ed., Marcel Dekker, Inc., New York (1975), pp. 451-454.

Harlow et al., Antibodies A Laboratory Manual, Cold Spring Laboratory (1988), pp. 547-549.

Pourfarzaneh et al., "Use of magnetisible particles in solid-phase immunoassay." In *Methods of Biochemical Analysis*. Glick, D., ed. 28, John Wiley, New York (1981).

Pourfarzaneh et al., Cortisol Directly Determined in Serum by Fluoroimmunoassay with Magnetizable Solid Phase, Clin. Chem., vol. 26(6): 730-33 (1980).

Kamel et al. Magnetizable Solid-Phase Fluroimmunoassay of Phenytoin in Disposable Test Tubes, Clin. Chem., vol. 26(9): 1281-84 (1980).

Falbe et al., Rompp Chemie Lexikon, $9^{th}$ Edition, Georg Thieme Verlag Stuttgart, pp. 669, 2560, 2561 (1989).

Alberts et al., Molekularbiologie der Zelle, pp. 99 and 1089 (1986).

Arnold et al., Biochemie, Springer-Verlag Berlin Heidelberg New York, p. 607 (1980).

De Boever et al., Direct Chemiluminescence Immunoassay for Estradiol in Serum, Clinical Chemistry, vol. 32(10): 1895-1900 (1988).

Bagazgoitia et al., Effect of Surfactants on the Intensity of Chemiluminescence Emission from Acridinium Ester Labelled Proteins, Journal of Bioluminescence and Chemiluminescence, 2:121-28 (1988).

Degan et al., A New Fluorescence Enhancement Solution for Europium-based Time-resolved Fluroimunnoassays, Journal of Bioluminescence and Chemiluminescence, 5:207-12 (1990).

Jürgen Falbe and Manfred Regitz, Römpp, 10:927, 3506-07, (1991).

Masseyeff et al., The Art of Assay Design in Heterologous Enzyme Immunoassay, Immunoenzymatic Techniques, pp. 139-155 (Mar. 16-18, 1983).

Pesce et al., Theories of Immunoassay Employing Labeled Reagents with Emphasis on Heterogenous Enzyme Immunoassay, Immunoenzymatic Techniques, p. 132 (Mar. 16-18, 1983).

Roitt et al., Antigen-Antikörper-Reaktionen, In Kurzes Lehrbuch der Immunologie, Georg Thieme Verlag, Stuttgart, p. 59 (1987).

Robinson et al., The Properties of Magnetic Supports in Relation to Immobilized Enzyme Reactors, Biotechnology and Bioengineering, XV:603-06 (1973).

Lubert Stryer, Biochemie, pp. 929, 938-29, and Figure 2.42, (1992).

* cited by examiner

METHODS FOR DETERMINATION OF AN ANALYTE

This application is a continuation of application Ser. No. 08/466,881, filed Jun. 6, 1995, issued as U.S. Pat. No. 7,029,856 B1 on Apr. 18, 2006, which is a continuation of application Ser. No. 08/173,939, filed Dec. 28, 1993, abandoned, which is a continuation of application Ser. No. 07/805,688, filed Dec. 12, 1991, abandoned, which claims the benefit of German application no. P 40 41 080.3, filed Dec. 21, 1990.

The invention relates to analytical methods in which the partition of a labeled substance between a liquid and a solid phase is determined. The assays include solid-phase reagents which can be particulate or monolithic such as, for example, a coated tube. Assays of this type are known per se to the person skilled in the art and include immunoassays and immunometric assays.

In many cases incubation of the reagents is followed by removal of the solid phase from the liquid phase, so-called heterogeneous or solid-phase immunometric determinations. A particulate solid phase can be removed from the liquid phase by sedimentation, centrifugation, filtration or a magnetic field.

Solid phases for use in such immunoassays are likewise known to the person skilled in the art and described in the literature, see, for example, VOLLER, A. et al., Bull. World Health Org. 53, 55-65 (1976).

Magnetizable particles which can be suspended but are insoluble in the liquid phase have the advantage that they can rapidly be removed from the liquid phase in a magnetic field.

Methods for the determination of analytes using magnetic particles are described, for example, in U.S. Pat. Nos. 4,554,088, 3,933,997 and in European Patent Application EP 0 136 126. Substances labeled with radioisotopes are employed for determination of an analyte in these methods.

These methods described above have the crucial disadvantage that they are confined to the use of radioisotopes with their known potential hazards and the consequent difficulties with handling and waste disposal.

Figure 1:
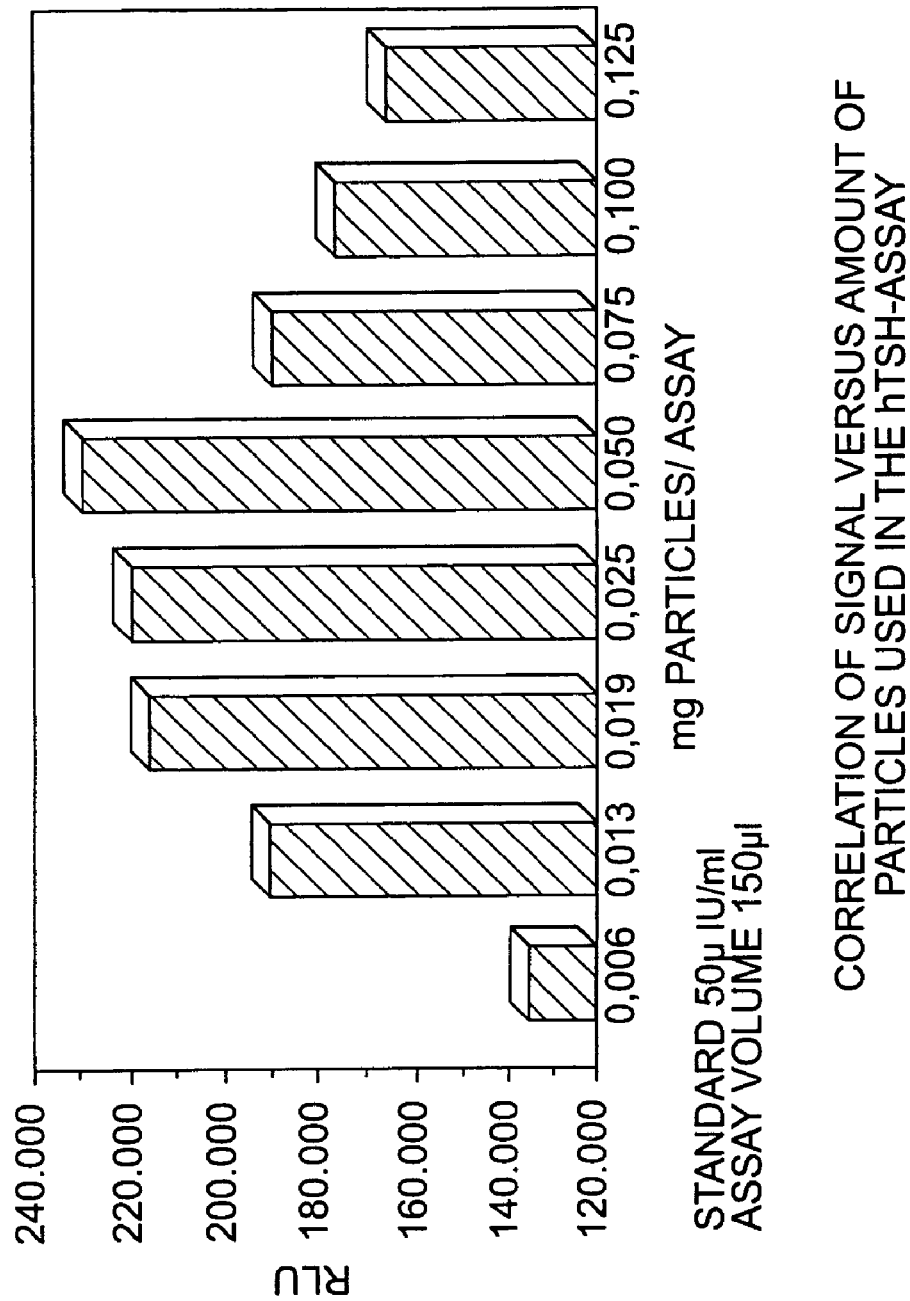
FIG. 1 shows a correlation between signal versus amount of particles used in an assay measuring human thyroid stimulating hormone (hTSH).

Now widely used as alternative to the use of radioisotopes as label are enzymes and thus enzyme immunoassays. In this method the reagent to be labeled is linked to an enzyme and, after the formation of the solid-phase receptor/analyte complex or of the solid-phase receptor/analyte/receptor complex, an incubation is carried out with a substrate of the enzyme. The enzyme reaction now produces a colored, luminescent or fluorescent derivative of the substrate. After completion of the reaction it is the absorption, luminescence or fluorescence which is measured in place of the radioactivity.

Suitable particles which can be removed magnetically have an intrinsic color owing to their content of, for example, iron oxide particles. They absorb light as a function of their size and their magnetite content. This intrinsic absorption by the particles reduces non-specifically the signal in a measurement of absorption, luminescence or fluorescence. The extent of the absorption of light depends, inter alia, on the amount of magnetic particles employed.

The dependencies also apply, of course, although the extent differs, to particles not amenable to magnetic attraction.

The Patent Application EP 0 177 191 describes a heterogeneous enzyme immunoassay with magnetic particles as solid phase, with an enzyme/analyte conjugate and with a chromogenic substrate as signal-emitting reagent. The magnetic particles must be removed before measuring the absorption. The disadvantage of this method is the necessity for an additional further incubation step of, normally, 20-60 min to generate the signal. The method thus requires a considerably greater expenditure of time and effort than comparable methods which use radioisotopes. Another disadvantage is based on the fact that this method cannot be used for heterogeneous immunoassays which use a direct chemiluminescent or fluorescent label.

This is not possible in enzyme-enhanced luminescence systems as are disclosed in the literature and employed, for example, in the Patent Application EP 0 149 565. A peroxidase is used therein to stimulate a substrate of the luminol type to emit light. Removal of the particles which carry the complex of receptor and enzyme in this method means that chemiluminescence generation is no longer possible and thus no signal can be measured either.

U.S. Pat. No. 4,576,912 discloses a method in which a fluorophore is coupled via a carrier molecule to the specific binding partner. The fluorophore is liberated after removal of the unbound conjugate by chemical or enzymatic hydrolysis of the carrier molecule, and this hydrolysis typically takes 60 min. Chemiluminescent labels are not considered in the patent.

The method described in EP 0 149 565 represents the state of the art. This patent application describes the measurement of chemiluminescence and fluorescence in the presence of suspended magnetic particles. It is shown therein that there is a narrow concentration range for the magnetic particles within which it is possible to carry out an assay despite the absorption of light (see also FIG. 1). However, as the present invention shows, this does not exhaust the advantages of the magnetic particle technology such as large surface area and short diffusion pathways.

It has now been found, surprisingly, that it is possible by adding suitable substances to measure without interference the signal of the labeled reagents by detaching the label and after removal of the solid phase. The measured signal shows a strict relation to the concentration of the analyte employed.

Figure 2:
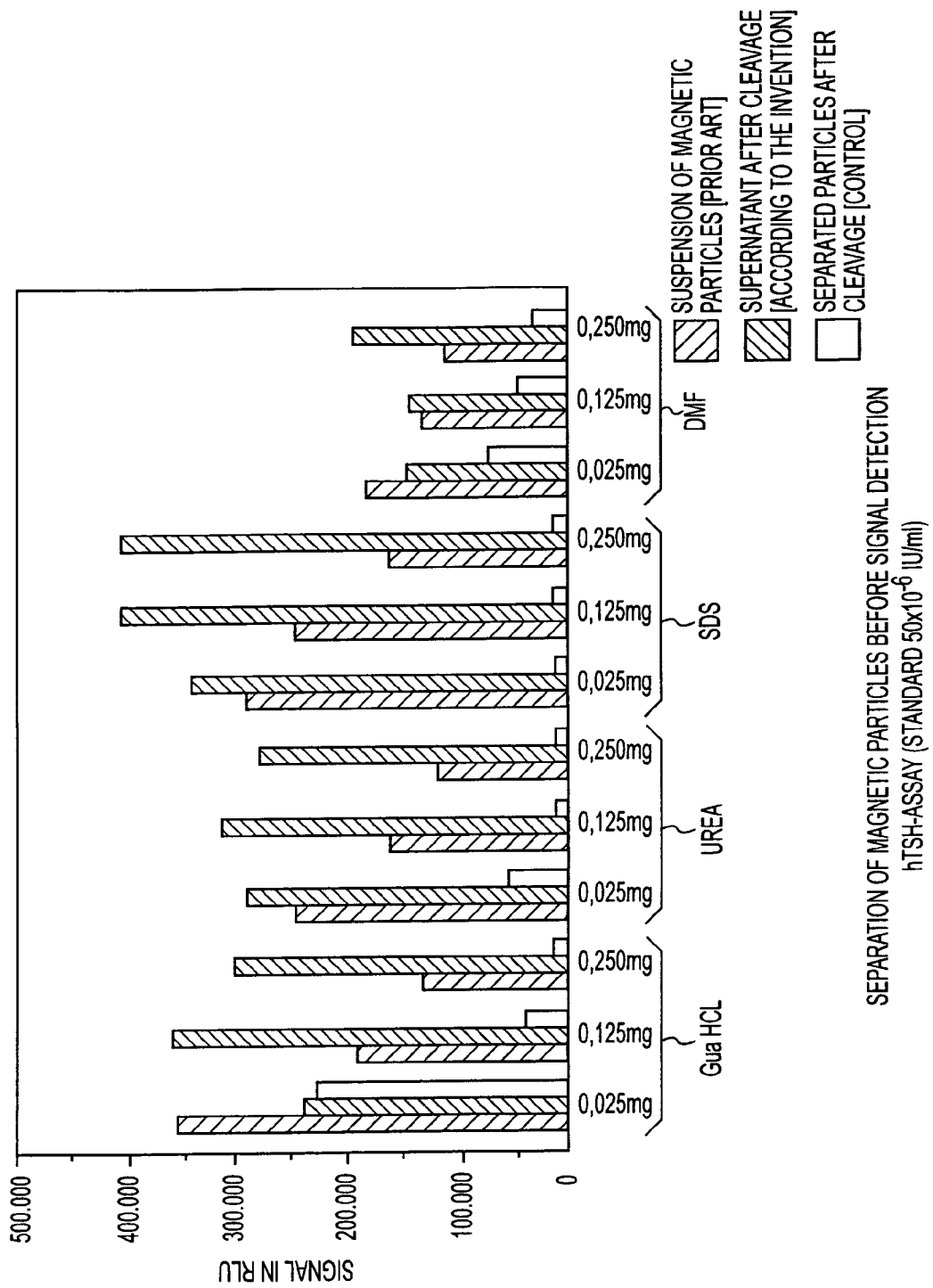
FIG. 2 shows in graphical form the data appearing in Table 1 of Example 2.

The method according to the invention achieves a distinctly greater signal yield and improved signal dynamics than the method described in EP 0 149 565 (see also FIG. 2).

Without wishing to specify a particular mechanism of action hereby, we assume that the substances according to the invention split the label-carrying complex with the solid phase and liberate the label in a suitable form.

The present invention now makes it possible to employ the solid phase in high concentrations. The enlarged surface area also makes it possible to employ the solid-phase receptor in a larger excess compared with the analyte. Furthermore, the diffusion pathways are considerably shortened. The two effects have a beneficial influence on the position of the equilibrium and on the reaction kinetics of an assay.

The present invention now relates to a heterogeneous immunochemical method for the determination of an analyte in a liquid medium, which contains the following steps in the method:

incubation of a sample which contains the analyte with the magnetically attractable solid-phase reagent and with the reagent labeled with a luminophore or fluorophore in a reaction vessel, the labeled reagent being partitioned between liquid phase and the magnetically attractable particles as a function of the concentration of the analyte, removal of the liquid phase from the solid-phase particles, resuspension of the particles in a reagent A, removal of the particles, elicitation and measurement of the luminescence or fluorescence reaction in the supernatant, where reagent A is suitable for detaching the label from the solid phase.

It is possible, where appropriate, for washing steps to be inserted between the individual steps.

The process is, in principle, also suitable for systems which, for example, determine enzyme activities or radioactivity as marker, however it is particularly advantageous in connection with a fluorescent or chemiluminescent label, and a chemiluminescent label is preferred.

Various chemiluminescence systems are described in the literature, and of these luminol, isoluminol and acridinium derivatives have acquired major importance. Luminol and isoluminol derivatives are described by H. R. Schroeder et al. "Methods in Enzymology" Academic Press Inc, New York, Vol LVII 424 et seq. The use of the acridinium derivatives as labeling substances is described by Weeks et al. (Clin. Chem 29/8, 1983, 1474-1479). The chemiluminescence of acridinium derivatives can be initiated by addition of alkaline $H_2O_2$ and measured within a few seconds.

These compounds have the advantage as labeling reagent that no further incubation step is necessary to elicit the signal, in contrast to the enzyme-enhanced luminescence systems. Furthermore, the acridinium compounds are stable to the reagents used herein.

Preferred chemiluminescent labels are the acridinium compounds described in EP 0 257 541 and EP 0 330 050.

The exact construction of the magnetically attractable particles used herein is known per se to the person skilled in the art and substantially unimportant in respect of the invention, preference being given to superparamagnetic particles which can advantageously be designed as composite particles or pure magnetite particles. It is also possible in principle for non-magnetizable particles to be employed, in which case the separation method must be appropriate for the particular particle, for example centrifugation or chromatography. Such particulate solid phases are also known to the person skilled in the art, such as, for example, latex particles which can be colored or uncolored.

The particles preferably have a size of 0.1-5.0 µm, and a range of 0.2-2.5 µm is particularly preferred, very particularly preferably 0.2-1.0 µm.

It is advantageous to employ in an assay small particles which, for the same total mass of particles, have a large number and a large surface area overall. A large number of particles means that the distance from particle to particle in a given volume is very small, the consequence being that the diffusion pathways of the dissolved analytes and of the labeled substance to the particle surface area are very small. There is accordingly an increase in the rate of the reaction leading to the formation of the receptor complexes bound to the solid phases. Moreover, the larger total surface area of the solid phase makes it possible to achieve an increased receptor concentration. High receptor concentrations result in extensive binding of the analyte and likewise in an increase in the reaction rate.

Small magnetically removable composite particles do, however, require a large proportion of magnetizable material in order to be able to be removed from the reaction solution within practicable times. The absorption of light by a particle suspension depends, inter alia, on the nature, on the size, on the content of magnetic material and on the concentration of the particles employed. If, as described in the state of the art, the signal is measured in the presence of the suspended particles, the measurable signal in an assay for the determination of, for example, TSH in serum then passes through a maximum as the amount of particles per mixture increases. When the amount of particles which is optimal under these conditions is exceeded, the increase in the absorbed amount of light exceeds the additional chemiluminescence obtained by the increase in the binding of labeled reagent (FIG. 1).

The use of magnetically removable particles in a sufficiently wide concentration range is therefore made possible only by the method according to the invention.

The detachment reagents used in this invention meet the following requirements:

elimination of at least one intermolecular linkage which is essentially composed of hydrogen bonds and ionic, hydrophobic and van der Waals interactions no impairment of the chemiluminescence reaction by absorption of light no quenching of the excited state of the luminophore no reaction with alkaline $H_2O_2$ solution no impairment of the magnetic removability of the magnetic particles no dissolution or aggregation of the magnetic particles.

Reagents which meet these conditions include, for example, chaotropic reagents, ionic detergents, some organic solvents, and buffer substances which are suitable for adjusting a pH in the range 1.5-3. Besides the reagents listed hereinafter by way of example, a large number of other reagents and their combinations which meet the stated requirements are conceivable. Some of them have been employed in the examples.

|  | Preferred | Particularly preferred Concentration range |
| --- | --- | --- |
| chaotropic reagents: | | |
| KSCN | 2 mol/l-sat.*) | 3–5 mol/l |
| Guanidinium hydrochloride | 3 mol/l-sat. | 3–5 mol/l |
| very particularly preferred | | 3 mol/l, pH 4 |
| $CaCl_2$ | 1 mol/l-sat. | 1–3 mol/l |
| $NaClO_4$ | 1 mol/l-sat. | 1–3 mol/l |
| Tetra-N-butylammonium chloride | 0.01% (w/v)-sat. | 0.01–1% (w/v) |
| Tetramethylammonium chloride | 0.01% (w/v)-sat. | 0.01–1% (w/v) |
| Urea | 3–8 mol/l | 4–7 mol/l |
| very particularly preferred | | 5 mol/l, pH 4 |
| ionic detergents: | | |
| SDS (Na dodecyl sulfate) | 0.01–20% (w/v)-sat. | 0.01–10% (w/v) |
| very particularly preferred | 1% (w/v) | in 10 mmol/l sodium phosphate, pH 6 |
| organic solvents: | | |
| Propionic acid | 0.1–30% (w/v) | 1–10% (w/v) |
| Ethylene glycol | 30–80% (w/v) | 40–60% (w/v) |
| DMF (dimethylformamide) | 40–90% (v/v) | 50–70% (v/v) |
| very particularly preferred | | 60% (v/v) |
| buffer: | | |
| Glycine pH 2 | 0.1 mol/l-sat. | 0.5–1 mol/l |
| very particularly preferred | | 0.5 mol/l, pH 2 |

*)sat. = saturated solution

These reagents can be employed singly or in combination.

It is in principle easy for the person skilled in the art to establish the optimal conditions for a particular substance or combination of substances by a few experiments in which he employs various concentrations.

The embodiments indicated in the examples are particularly preferred.

The invention can in principle be used in methods in which the partition of a labeled reagent between a liquid and a solid phase is determined.

In the course of this method, the solid phase, analyte and labeled reagent are incubated, either simultaneously or consecutively, for a suitable time. After the incubation the solid phase is removed and then suspended in the detachment reagent and incubated for a short time. The particles are again removed and the supernatant is measured. If a large number of samples is investigated at the same time, the sequence of steps is typically as follows:

A. Pipetting of suspended, magnetically attractable particles, samples, standards and labeled reagent into reaction vessels.
B. Incubation of the vessels containing the reaction mixture at the required temperature for a defined time.
C. Removal of the magnetic particles with an arrangement of magnets suitable for the vessels used.
D. Removal of the supernatants by aspiration with suitable pipettes, pumps or vacuum.
E. Repeated addition and removal by aspiration of washing buffer.
F. Removal or switching off of the magnetic field used to remove the magnetizable particles, and resuspension of the magnetic particles in the detachment reagent.
G. Removal of the particles with the magnet system, transfer of the supernatant into a suitable vessel and measurement of the label.

The claims form part of the disclosure.

The following examples serve to illustrate the invention but do not restrict it in any way. Unless otherwise indicated, Estapor® particles (0.35 µm) supplied by Rhone-Poulenc are used as magnetically removable particles.

EXAMPLE 1

Determination of Human Thyroid Stimulating Hormone (hTSH) According to the State of the Art (Measurement in Suspension)

The following reagents were incubated together in polystyrene tubes:
0.006 mg; 0.013 mg; 0.019 mg; 0.025 mg; 0.050 mg; 0.075 mg; 0.1 mg and 0.125 mg of magnetically removable particles coated with a monoclonal anti-hTSH antibody,
100 µl of a solution 50 µIU/ml hTSH in human serum,
40 µl of a solution of a monoclonal antibody conjugated to an acridinium derivative,
suspension of the particles,
incubation of the suspension at 37° C. for 15 min,
removal of the particles with a separation system supplied by Gene-Trak, and removal of the supernatant by aspiration,
300 µl of washing buffer are added four times, and removed by aspiration again each time, to the removed particles,
the particles are then resuspended in 100 µl of washing buffer,
and transferred into polypropylene tubes (1 ml). These tubes are placed in polystyrene tubes (5 ml). The chemiluminescence is elicited by addition of 300 µl of 0.1 N nitric acid and 0.5% $H_2O_2$ and 300 µl of 0.25 N sodium hydroxide solution and measured in a luminescence measuring apparatus supplied by Berthold (Model LB952T) (see FIG. 1).

EXAMPLE 2

Determination of Human Thyroid Stimulation Hormone (hTSH)

The following reagents were incubated together in polystyrene tubes:
0.025 mg; 0.125 mg and 0.250 mg of magnetically removable particles coated with a monoclonal anti-hTSH antibody,
100 µl of a solution 50 µIU/ml hTSH in human serum,
40 µl of a solution of a monoclonal antibody conjugated to an acridinium derivative,
suspension of the particles,
incubation of the suspension at 37° C. for 15 min,
removal of the particles with a separation system supplied by Gene-Trak, and removal of the supernatant by aspiration,
300 µl of washing buffer are added four times, and removed by aspiration again each time, to the removed particles,
the particles are then resuspended in 100 µl of removal reagent, and then
 a) the suspension is employed for measurement
 b) the detached magnetic particles are removed and the supernatant is employed for measurement
 c) the removed magnetic particles from (b) are resuspended in 100 µl of washing buffer and this suspension is employed for measurement,
the sample employed for measurement is transferred into polypropylene tubes (1 ml). The tubes are placed in polystyrene tubes (5 ml). The chemiluminescence is elicited by addition of 300 µl of 0.1 N nitric acid and 0.5% $H_2O_2$ and 300 µl of 0.25 N sodium hydroxide solution and measured.

TABLE 1

Removal of the magnetic particles before signal detection [hTSH assay (signal in RLU)]

| | Measurement in suspension | Supernatant after detachment and removal | Removed magnetic particles (resuspended) |
| --- | --- | --- | --- |
| 1) GuaHCl | | | |
| 0.025 mg | 349,921 | 236,317 | 223,615 |
| 0.125 mg | 188,512 | 353,445 | 37,410 |
| 0.250 mg | 132,766 | 295,127 | 10,692 |
| 2) Urea | | | |
| 0.025 mg | 240,053 | 286,195 | 49,715 |
| 0.125 mg | 158,493 | 305,402 | 5,961 |
| 0.250 mg | 117,389 | 270,993 | 3,778 |
| 3) SDS | | | |
| 0.025 mg | 282,840 | 331,649 | 3,198 |
| 0.125 mg | 240,143 | 395,635 | 5,817 |
| 0.250 mg | 156,367 | 398,028 | 6,946 |
| 4) DMF | | | |
| 0.025 mg | 171,610 | 139,728 | 64,795 |
| 0.125 mg | 129,485 | 135,785 | 38,591 |
| 0.250 mg | 108,097 | 185,875 | 20,312 |

Detachment reagent:
1) Guanidinium HCl  3 mol/l, pH 4
2) Urea  5 mol/l, pH 4
3) SDS  1 g/100 ml of 10 mmol/l sodium phosphate buffer pH 6
4) DMF  60% (w/v)

These data are depicted as a graph in FIG. 2.

EXAMPLE 3

Determination of Human Thyroid Stimulating Hormone (hTSH)

The following reagents were incubated together in Flow tubes:
0.125 mg of magnetically removable particles coated with a monoclonal anti-hTSH antibody,
100 μl of a standard solution of hTSH in human serum,
40 μl of a solution of a monoclonal antibody conjugated to an acridinium derivative,
suspension of the particles,
incubation of the suspension at 37° C. for 15 min,
removal of the particles with a separation system supplied by Gene-Trak, and removal of the supernatant by aspiration,
300 μl of washing buffer were added four times to the removed particles,
the particles were then resuspended in 100 μl of removal reagent and subsequently placed in the separation system for 2 min,
the supernatant is removed and transferred into Flow tubes. The Flow tubes are placed in Sarstedt tubes. The chemiluminescence is elicited by addition of 300 μl of 0.1 N nitric acid and 0.5% $H_2O_2$ and 300 μl of 0.25 N sodium hydroxide solution and measured luminescence measuring apparatus.

TABLE 2

| Standard | | Removal of the particles RLU | No removal of the particles RLU |
|---|---|---|---|
| S0 | 0.0 μIU/ml | 273 | 445 |
| S1 | 0.14 μIU/ml | 1219 | 1149 |
| S2 | 0.47 μIU/ml | 3179 | 2060 |
| S3 | 1.5 μIU/ml | 9235 | 5621 |
| S4 | 4.8 μIU/ml | 31477 | 17078 |
| S5 | 14.2 μIU/ml | 96629 | 49972 |
| S6 | 50 μIU/ml | 304099 | 164966 |
| S7 | 100 μIU/ml | 496261 | 276073 |

Figure 3:
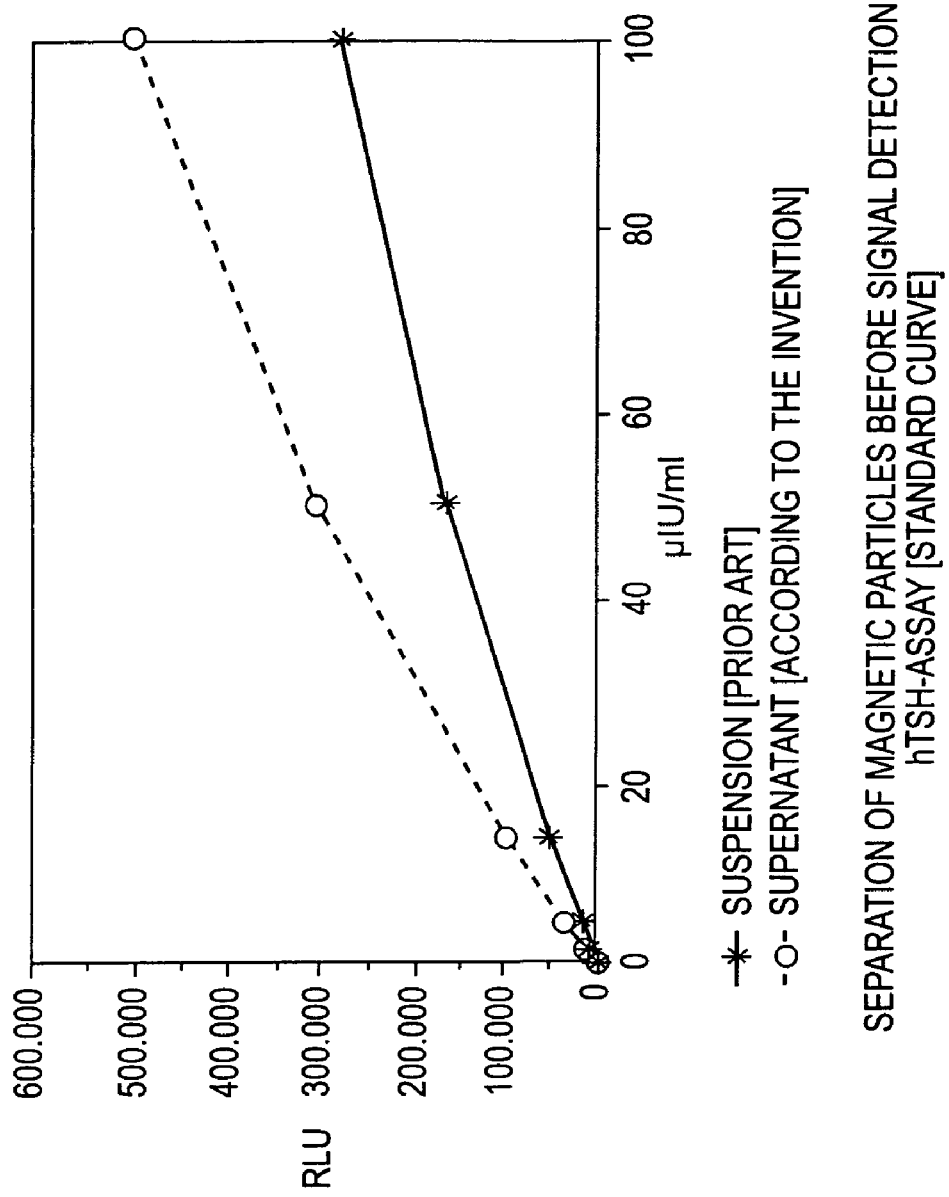
FIG. 3 shows in graphical form the data appearing in Table 2 of Example 3.

These data are depicted as a graph in FIG. 3.

The invention claimed is:

1. A heterogeneous immunochemical method for the determination of an analyte in a sample in a liquid medium, comprising:
a) incubating the sample in a reaction vessel with a particulate solid-phase on which a first binding partner which specifically binds to the analyte is immobilized; wherein the particles of the particulate solid phase have a size of 0.1-5.0 μm; and with a second binding partner which specifically binds to the analyte, wherein a fluorescent or chemiluminescent label is conjugated to the second binding partner, and wherein after addition of the solid-phase and the second binding partner the solid-phase is suspended in the liquid medium, whereby the second binding partner is partitioned between the liquid medium and the particulate solid-phase and the solid-phase is subjected to magnetic or gravitational attraction to attract the solid-phase in the liquid medium to an interior surface of the reaction vessel;
b) removing the first liquid medium from the solid-phase prior to adding a second liquid medium to the solid-phase;
c) resuspending the solid-phase in the second liquid medium;
d) adding a reagent A, which causes a separation of the solid-phase and the label by elimination of at least one intermolecular linkage which is essentially composed of hydrogen bonds and ionic, hydrophobic and van der Waals interactions;
e) removing the solid-phase by magnetic or gravitational attraction; and
f) determining the amount of analyte in the sample, wherein the reagent A contains in aqueous solution one substance selected from the group of reagents consisting of:
a chaotropic agent, and
a buffer for adjusting the pH to a range of 1.5 to 3;
wherein a) through f) are performed in sequential order.

2. The method of claim 1, wherein the particulate solid-phase is magnetically attractable.

3. The method of claim 1, wherein the label is chemiluminescent.

4. The method of claim 1, wherein the reagent A contains said buffer for adjusting the pH to a range of pH 1.5 to 3 in a concentration of 0.1 to 1 mol/l; and an ionic detergent.

5. The method of claim 4, wherein the ionic detergent has a concentration of 0.01 to 10% (w/v).

6. The method of claim 4, wherein the ionic detergent is sodium dodecylsulfate.

7. The method of claim 4, wherein the buffer is glycine.

8. The method of claim 5, wherein said detergent concentration is 1% (w/v).

9. The method of claim 1, wherein the particles of the particulate solid phase have a size of 0.2-2.5 μm.

10. The method of claim 1, wherein the particles of the particulate solid phase have a size of 0.2-1.0 μm.

11. A heterogeneous immunochemical method for the determination of an analyte in a sample in a liquid medium, comprising:
a) incubating the sample in a reaction vessel with a particulate solid-phase on which a first binding partner which specifically binds to the analyte is immobilized; wherein the particles of the particulate solid phase have a size of 0.1-5.0 μm; and with a second binding partner which specifically binds to the analyte, wherein a fluorescent or chemiluminescent label is conjugated to the second binding partner, and wherein after addition of the solid-phase and the second binding partner the solid-phase is suspended in the liquid medium, whereby the second binding partner is partitioned between the liquid medium and the particulate solid-phase and the solid-phase is subjected to magnetic or gravitational attraction to attract the solid-phase in the liquid medium to an interior surface of the reaction sample;
b) removing the first liquid medium from the solid-phase prior to adding a second liquid medium to the solid-phase;
c) resuspending the solid-phase in the second liquid medium;
d) adding a reagent A, which causes a separation of the solid-phase and the label by elimination of at least one intermolecular linkage which is essentially composed of hydrogen bonds and ionic, hydrophobic and van der Waals interactions;
e) removing the solid-phase by magnetic or gravitational attraction; and f) determining the amount of analyte in the sample, wherein the reagent A contains in an aqueous solution one substance selected from the group of reagents consisting of:
KSCN,
guanidinium hydrochloride,
$NaClO_4$,
urea,
propionic acid,
dimethylformamide, and
glycine for adjusting the pH to a range of 1.5 to 3;
wherein a) through f) are performed in sequential order.

* * * * *